(12) United States Patent
Grashow

(10) Patent No.: US 10,459,232 B2
(45) Date of Patent: Oct. 29, 2019

(54) AUGMENTED REALITY PATIENT INTERFACE DEVICE FITTING APPARATUS

(71) Applicant: KONINKLIJKE PHILIPS N.V., Eindhoven (NL)

(72) Inventor: Jonathan Sayer Grashow, Cheswick, PA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/520,425

(22) PCT Filed: Oct. 10, 2015

(86) PCT No.: PCT/IB2015/057758
§ 371 (c)(1),
(2) Date: Apr. 20, 2017

(87) PCT Pub. No.: WO2016/063166
PCT Pub. Date: Apr. 28, 2016

(65) Prior Publication Data
US 2017/0315359 A1    Nov. 2, 2017

Related U.S. Application Data

(60) Provisional application No. 62/066,495, filed on Oct. 21, 2014.

(51) Int. Cl.
G02B 27/01    (2006.01)
A61M 16/06   (2006.01)
(Continued)

(52) U.S. Cl.
CPC ......... G02B 27/0172 (2013.01); A61M 16/06 (2013.01); A61M 16/0605 (2014.02);
(Continued)

(58) Field of Classification Search
CPC ............ G02B 27/0172; G02B 27/0179; G02B 2027/0178; A61M 16/06; G06F 19/00; G06T 19/00
See application file for complete search history.

(56) References Cited

U.S. PATENT DOCUMENTS 5,280,305 A * 1/1994 Monroe ................... A41G 7/00
347/129
8,254,637 B2 * 8/2012 Abourizk .............. A61M 16/06
356/601
(Continued)

FOREIGN PATENT DOCUMENTS

JP          2010131091 A    6/2010
WO         WO0146911 A1    6/2001
WO       WO2014180944 A1   11/2014

*Primary Examiner* — Grant Sitta
(74) *Attorney, Agent, or Firm* — Michael W. Haas

(57) ABSTRACT

An augmented reality apparatus for facilitating a patient interface device fitting process includes a device or system for providing a real-time image of the patient, and a processor apparatus structured to: (i) store a plurality of augmented reality component data files, each of the augmented reality component data files relating to either a structure or an aspect of one or more particular patient interface devices or a problem that may be encountered in the fitting process, and (ii) cause an augmented real-time image to be created and transmitted by the augmented reality apparatus by augmenting the real-time image using at least one of the augmented reality component data files.

14 Claims, 8 Drawing Sheets

(51) Int. Cl.
*G06F 3/01* (2006.01)
*G06T 19/00* (2011.01)
*G16H 40/63* (2018.01)
*G03B 21/26* (2006.01)
*G06F 19/00* (2018.01)

(52) U.S. Cl.
CPC ....... *G02B 27/017* (2013.01); *G02B 27/0179* (2013.01); *G06F 3/011* (2013.01); *G06F 19/00* (2013.01); *G06T 19/00* (2013.01); *G16H 40/63* (2018.01); *G02B 2027/014* (2013.01); *G02B 2027/0138* (2013.01); *G02B 2027/0178* (2013.01); *G02B 2027/0187* (2013.01); *G03B 21/26* (2013.01)

(56) References Cited

U.S. PATENT DOCUMENTS

| | | | | |
|---|---|---|---|---|
| 8,982,109 | B2* | 3/2015 | Vilcovsky | H04N 7/144 345/204 |
| 9,307,930 | B2* | 4/2016 | Todd | A61B 5/1075 |
| 9,361,411 | B2* | 6/2016 | Thiruvengada | G06F 17/5009 |
| 9,498,593 | B2* | 11/2016 | Karpas | B29C 33/52 |
| 2004/0039592 | A1* | 2/2004 | Shima | G06Q 30/0601 705/26.1 |
| 2004/0133604 | A1* | 7/2004 | Lordo | A61M 16/06 |
| 2004/0263863 | A1* | 12/2004 | Rogers | A61B 5/0064 356/602 |
| 2005/0083248 | A1* | 4/2005 | Biocca | A41D 31/0088 345/8 |
| 2006/0023228 | A1* | 2/2006 | Geng | A61B 5/411 356/601 |
| 2006/0235877 | A1 | 10/2006 | Richard | |
| 2008/0006273 | A1* | 1/2008 | Thornton | A61M 16/06 128/206.21 |
| 2008/0060652 | A1 | 3/2008 | Selvarajan | |
| 2011/0220112 | A1* | 9/2011 | Connor | A61M 16/06 128/206.24 |
| 2012/0245962 | A1 | 9/2012 | Smith | |
| 2012/0305003 | A1* | 12/2012 | Mark | A61M 16/06 128/206.24 |
| 2012/0313955 | A1* | 12/2012 | Choukroun | G06T 19/00 345/582 |
| 2013/0063487 | A1 | 3/2013 | Spiegel | |
| 2013/0229482 | A1* | 9/2013 | Vilcovsky | H04N 7/144 348/14.07 |
| 2014/0078137 | A1* | 3/2014 | Peddi | G09B 19/0038 345/419 |
| 2014/0139340 | A1* | 5/2014 | Yang | G09B 19/003 340/573.1 |
| 2014/0139551 | A1* | 5/2014 | McCulloch | G09G 5/377 345/633 |
| 2014/0191951 | A1* | 7/2014 | Ye | G06F 3/0304 345/156 |
| 2014/0278320 | A1* | 9/2014 | Wang | G06F 17/5009 703/11 |
| 2016/0035133 | A1* | 2/2016 | Ye | G06T 19/006 345/419 |
| 2017/0091535 | A1* | 3/2017 | Yu | G06K 9/00248 |
| 2018/0017815 | A1* | 1/2018 | Chumbley | G02C 5/12 |
| 2018/0028772 | A1* | 2/2018 | Davis | A61M 16/0644 |

* cited by examiner

AUGMENTED REALITY PATIENT INTERFACE DEVICE FITTING APPARATUS

CROSS-REFERENCE TO RELATED APPLICATIONS

This patent application claims the priority benefit under 35 U.S.C § 371 of international patent application no PCT/IB2015/057758, filed Oct. 10, 2015, which claims the priority benefit under 35 U.S.C. § 119(e) of U.S. Provisional Application No. 62/066,495 filed on Oct. 21, 2014, the contents of which are herein incorporated by reference.

BACKGROUND OF THE INVENTION

1. Field of the Invention

The present invention pertains to an apparatus for fitting a patient with a patient interface device for delivering a breathing gas to the airways of the patient, and, in particular, an augmented reality patient interface device fitting apparatus.

2. Description of the Related Art

There are numerous situations where it is necessary or desirable to deliver a flow of breathing gas non-invasively to the airway of a patient, i.e., without intubating the patient or surgically inserting a tracheal tube into the patient's esophagus. For example, it is known to ventilate a patient using a technique known as non-invasive ventilation. It is also known to deliver positive airway pressure (PAP) therapy to treat certain medical disorders, the most notable of which is obstructive sleep apnea (OSA). Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible sealing cushion on the face of a patient. The mask component may be, without limitation, a nasal mask that covers the patient's nose, a nasal cushion having nasal prongs that are received within the patient's nares, a nasal/oral mask that covers the patient's nose and mouth, or a full face mask that covers the patient's face. Such patient interface devices may also employ other patient contacting components, such as forehead supports, cheek pads and chin pads. The patient interface device is connected to a gas delivery tube or conduit and interfaces the ventilator or pressure support device with the airway of the patient so that a flow of breathing gas can be delivered from the pressure/flow generating device to the airway of the patient. It is known to maintain such devices on the face of a wearer by a headgear having one or more straps adapted to fit over/around the patient's head.

Because patient interface devices are typically worn for an extended period of time, a variety of concerns must be taken into consideration. For example, in providing CPAP to treat OSA, the patient normally wears the patient interface device all night long while he or she sleeps. One concern in such a situation is that the patient interface device needs to be as comfortable as possible, otherwise the patient may avoid wearing the interface device, defeating the purpose of the prescribed pressure support therapy. Another concern is that an improperly fitted patient interface device can include gaps between the patient interface device and the patient that cause unwanted leakage. Thus, it is desirable to select a patient interface device that properly fits a patient.

A variety of different types or styles of patient interface devices are available. Additionally, a variety of different sizes of each type and style of patient interface device are available. Thus, the total number of distinct patient interface devices available to a patient can become quite large.

Caregivers have generally assisted patients with the selection of a suitable patient interface device. The caregiver can take into account the patient's condition and preferences to narrow down the list of potential patient interface devices. The caregiver can also estimate the proper size of the patient interface device or have the patient try on several patient interface devices to determine the correct size. However, these methods can be time consuming, wasteful (actual devices may need to be opened and tried on) and, depending largely on the knowledge and experience of the caregiver, inaccurate.

SUMMARY OF THE INVENTION

In one embodiment, an augmented reality apparatus for facilitating a patient interface device fitting process is provided. The apparatus includes means for providing a real-time image of the patient, and a processor apparatus (8) structured to: (i) store a plurality of augmented reality component data files, each of the augmented reality component data files relating to either a structure or an aspect of one or more particular patient interface devices or a problem that may be encountered in the fitting process, and (ii) cause an augmented real-time image to be created and transmitted by the augmented reality apparatus by augmenting the real-time image using at least one of the augmented reality component data files.

In another embodiment, an augmented reality patient interface device fitting method is provided. The method includes storing a plurality of augmented reality component data files, each of the augmented reality component data files relating to either a structure or an aspect of one or more particular patient interface devices or a problem that may be encountered in the fitting method, providing a real-time image of a patient, and creating and transmitting an augmented real-time image by augmenting the real-time image using at least one of the augmented reality component data files.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
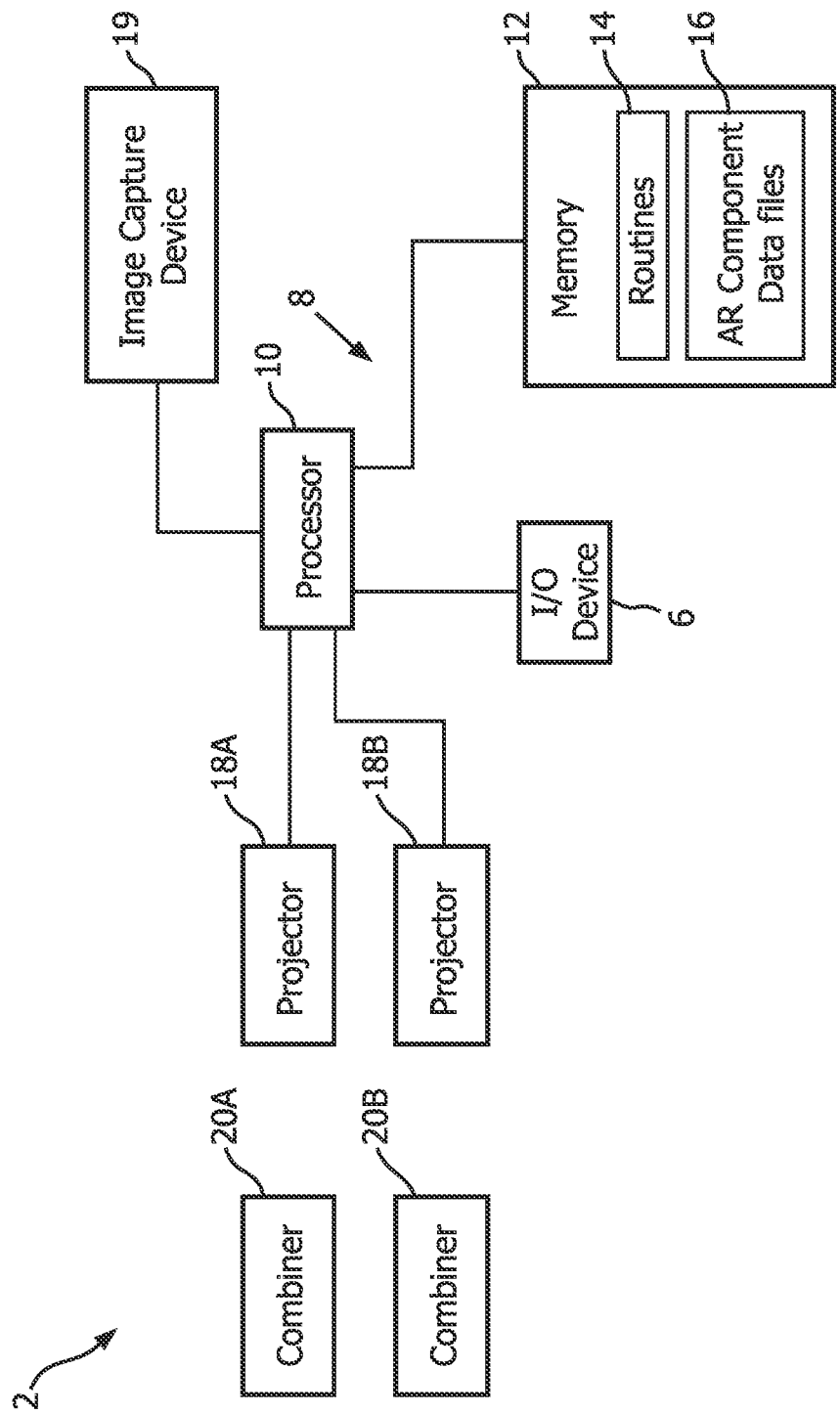
FIG. 1 is a block diagram and FIG. 2 is an isometric view of an AR apparatus for fitting a patient with a patient interface device according to one non-limiting exemplary embodiment of the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As used herein, the term "real-time" shall mean a response that appears to take place instantaneously or in the same timeframe as its real world counterpart action, process or event.

Augmented reality (AR) is a real-time (i.e., live) direct or indirect view of a physical, real-world environment whose elements are augmented (or supplemented) by computer-generated sensory input such as sound, video, graphics or other visual data or GPS data. Since the augmentation is done in real-time, AR technology functions by enhancing one's current perception of reality.

Currently, there are two basic options for combining real and the virtual (computer generated) elements to implement an AR system with augmented visuals: (i) optical systems, and (ii) video systems. Optical systems work by placing one or two optical combiners in front of the user's eyes. The combiners are partially transmissive, so that the user can look directly through them to see the real world, and partially reflective, so that the user can also simultaneously see virtual mages bounced off of the combiners from a projection system. Video systems use a closed view display apparatus in conjunction with one or two head mounted video cameras. The video cameras capture the user's view of the real world, and video from these cameras is combined with virtual, computer generated images to blend the real and the virtual into augmented image data. The augmented image data is sent to the closed view display apparatus to be viewed by the user.

As described in greater detail herein, the disclosed concept provides a number of AR apparatus implementations that are structured to facilitate and improve the patent interface device fitting process. For example, the disclosed concept would allow clinicians to visualize in real-time different patient interface device geometries and styles in real-time directly on the patient's face to assess sizing, fit and potential problems. An AR apparatus as described herein would thus be much more effective and informative than a sizing gauge or similar fitting tool since the entire interface device can be visualized in real-time with respect to the patient's facial geometry rather than just measuring a few discrete landmarks on the patient's face. The clinician could try different sizes and/or styles of interface devices on the patient virtually without needing to open any physical product (which wastes product). Thus, an AR apparatus as described herein would provide a much more natural and intuitive way to view and fit a patient interface device on a person's face/head.

Figure 2:
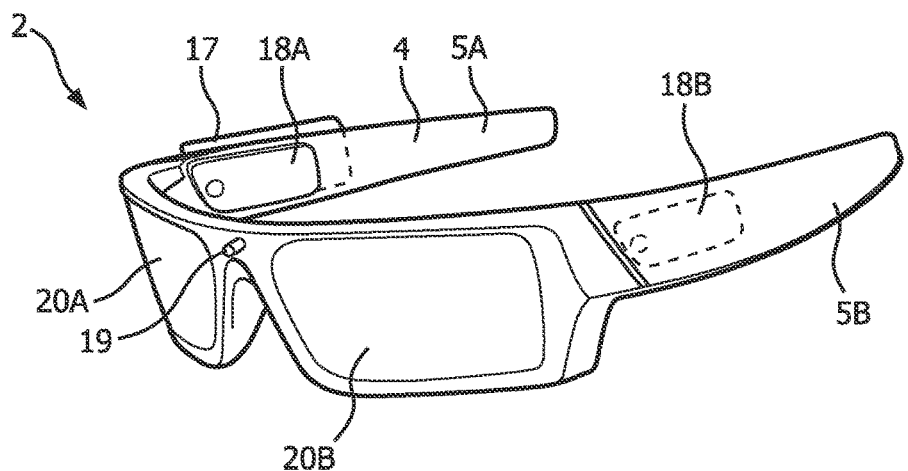

FIG. 1 is a block diagram and FIG. 2 is an isometric view of an AR apparatus 2 for fitting a patient with a patient interface device according to one non-limiting exemplary embodiment of the present invention. As seen in FIG. 2, AR apparatus 2 of this non-limiting, exemplary embodiment is an optical system that is implemented in the form of a pair of eyeglasses having a frame member 4 having earpieces 5A and 5B. Referring to FIG. 1, AR apparatus 2 includes an input/output device 6 (which may be, for example and without limitation, a number of buttons, a touchpad, a voice recognition interface, or an eye tracking system that would track the user's eyes in order to select options on a menu displayed by a projector (such as one of the projectors 18A and 18B described below) and a processor apparatus 8. A user is able to provide input (e.g., various commands) into processor apparatus 8 using input apparatus 6, and processor apparatus 8 provides control signals to control operation of AR apparatus 2 as described in detail herein.

Processor apparatus 8 comprises a processor 10 and a memory 12. Processor 10 may be, for example and without limitation, a microprocessor (µP), a microcontroller, or some other suitable processing device, that interfaces with memory 12 (which may be separate from or included as part of processor 10). Memory 12 can be any of one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory. Processor apparatus 8 may also employ cloud-based memory and processing and/or connectivity to a base station that includes memory and processing capabilities.

Memory 12 has stored therein a number of routines 14 that are executable by processor 10. One or more of the routines implement (by way of computer/processor executable instructions) a system for controlling AR apparatus 2 to facilitate the fitting of patent interface devices as described herein. Memory 12 also has stored therein a database of a plurality of AR component data files 16. Each AR component data files 16 comprises electronic data that may be used to augment the user's (e.g., clinician's) view of the physical, real-world environment during the mask fitting process. Such AR component data files 16 may include, for example and without limitation, data representing (i) a number of 2D or 3D patient interface device images that may be rendered on the real-world view of a patient's face, (ii) a number contact region images showing where various patient interface devices would actually contact the wearer's face that may be rendered on the real-world view of a patient's face, or (iii) a number of informational tags that may be rendered on the real-world view of a patient's face that, for example and without limitation, indicate for the clinician potential problems areas on the patient's face/head or instructions for using a particular patient interface device.

In the exemplary embodiment, processor apparatus 8 and input/output device 6 are housed by a housing member 17 that is coupled to the exterior surface of earpiece 5A.

AR apparatus 2 also includes a first video projector 18A and a second projector 18B, an image capture device 19, and a first combiner 20A and a second combiner 20B. Image capture device 19 is any device capable of capturing an image in digital form, such as a CCD camera or an analog camera coupled to an A/D converter. As seen in FIG. 2, image capture device is mounted on a front surface of frame member 4 at a generally central location. First combiner 20A and second combiner 20B in the illustrated embodiment each comprise a lens member that is supported by frame member 4 and that has an rear/inward facing surface that is reflective and is structured to direct reflected images to a corresponding one of eyes of the wearer of AR apparatus 2. Video projector 18A is coupled to the interior surface of earpiece 5A and video projector 18B is coupled to the interior surface of earpiece 5B. Video projectors 18A and 18B and image capture device 19 are also operatively coupled to processor apparatus 8 by suitable wiring (not shown) running along and/or within frame member 4 and are controlled by processor apparatus 8 to project images based on the AR component data files 16 onto the combiners 20A and 20B. The projected images are generated by processor apparatus 8 such that they will be appropriately located and aligned on combiners 20A and 20B based on a real-time image captured by image capture device 19. Thus, AR apparatus 2 is structured to implement an optical AR system wherein real world views through combiners 20A and 20B may be augmented in real-time using images based on the AR component data files 16.

Figure 3:
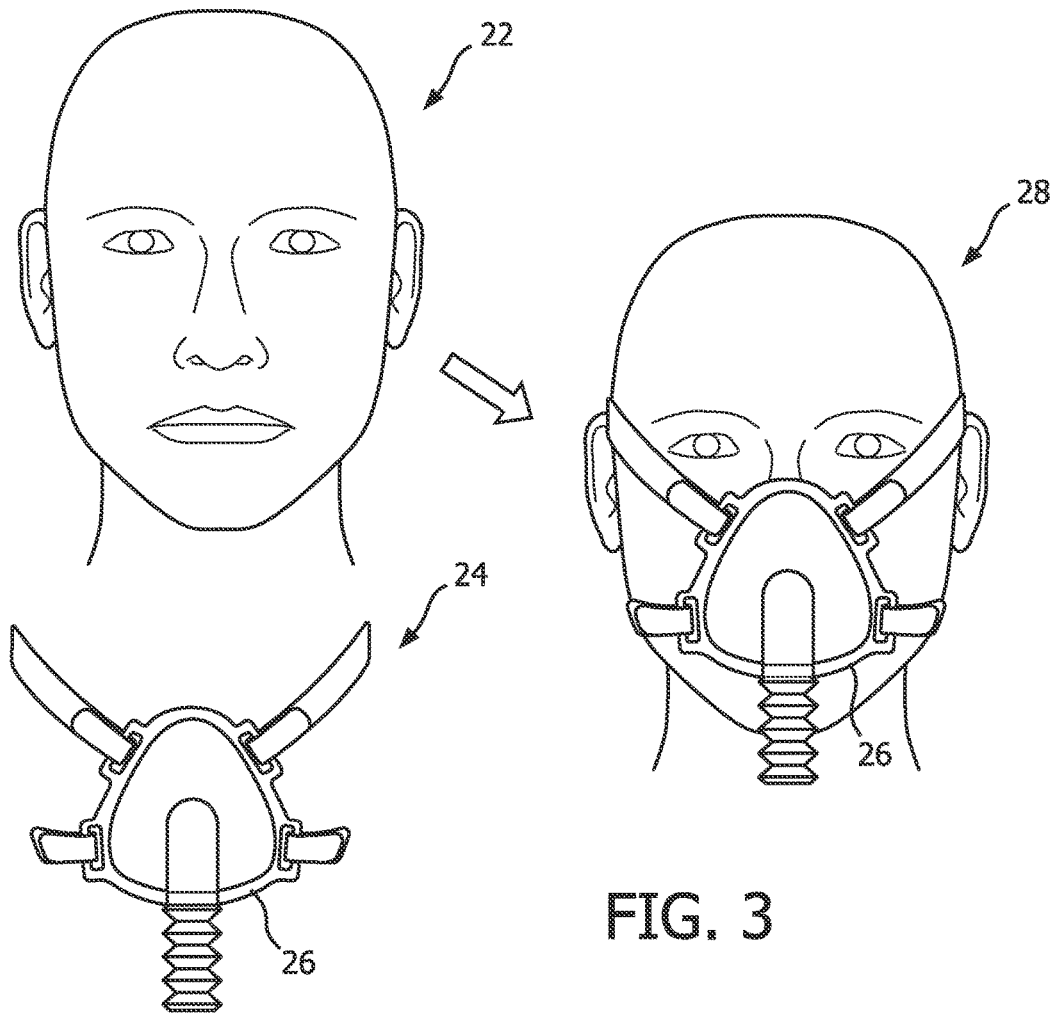
FIGS. 3-7 are schematic representations demonstrating the implementation of the AR apparatus of FIGS. 1 and 2 according various exemplary embodiments.

FIG. 3 is a schematic representation demonstrating the implementation of AR apparatus 2 according to one exemplary embodiment wherein the AR component data files 16 comprise data representing a number of 2D or 3D patient interface device images. As seen in FIG. 3, reference numeral 22 represents the un-augmented real world view that exists in an environment and that would be viewed by a user of AR apparatus 2 without the assistance of AR apparatus 2. As will be appreciated, the view 22 is what is transmitted to and through combiners 20A and 20B from the front side thereof. Reference numeral 24 represents an image of a patient interface device 26 that is projected by projectors 18A and 18B onto combiners 20A and 20B based on a particular AR component data file 16. Reference numeral 28 represents an augmented image that is transmitted from the rear of combiners 20A and 20B and that is therefore viewed by the user of AR apparatus 2. In the image 28, the view 22 and the image 24 have been combined. The particular AR component data file 16 that is used to generate the image 24 may be selected by the user using input/output apparatus 6, and thus the implementation of AR apparatus 2 just described may be used by a clinician to visualize in real-time different patient interface device geometries and styles directly on the patient's face to assess sizing, fit and potential problems.

Figure 4:
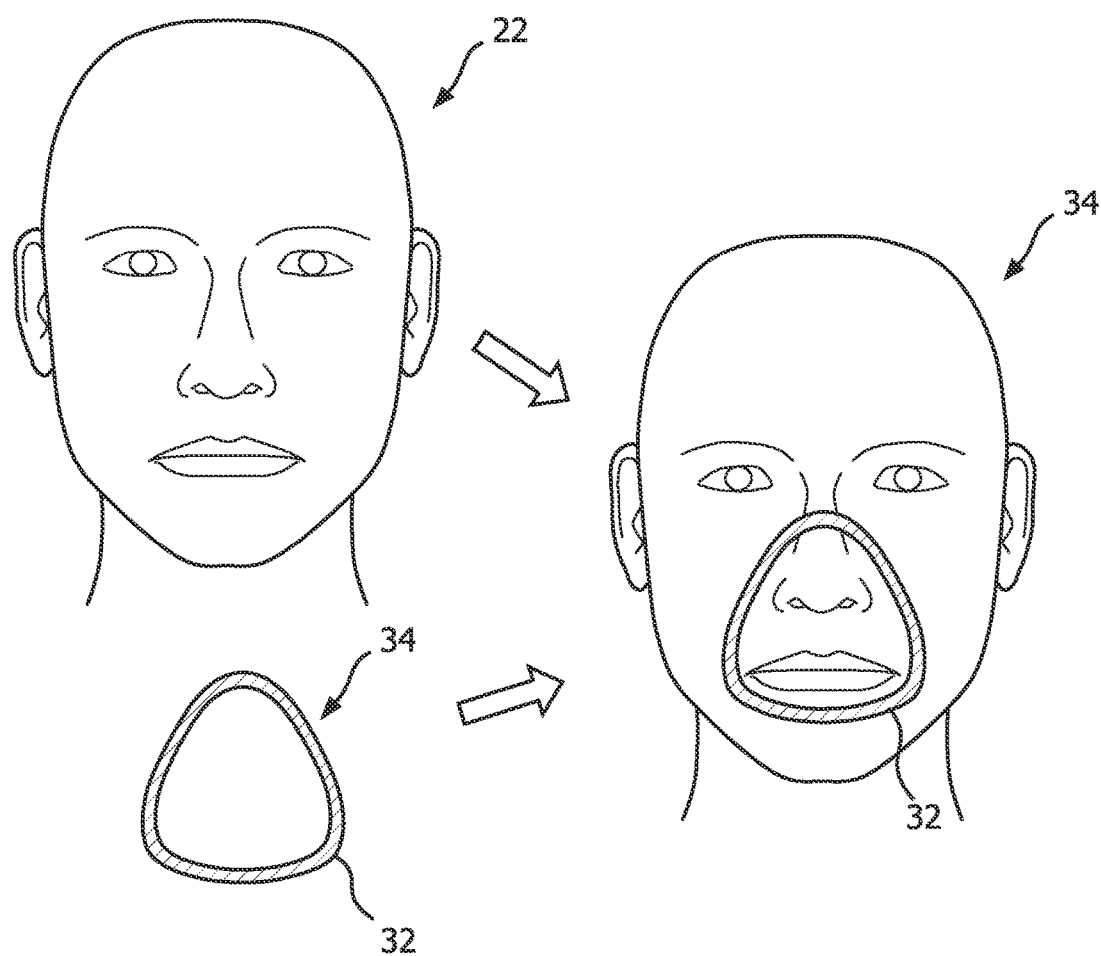

FIG. 4 is a schematic representation demonstrating the implementation of AR apparatus 2 according to another exemplary embodiment (which may be used alone or in combination with the embodiment of FIG. 3) wherein the AR component data files 16 comprise data representing a number contact region images showing the locations where various patient interface devices would actually contact the wearer's face. As seen in FIG. 4, reference numeral 22 represents the un-augmented real world view described above. Reference numeral 30 represents an image of a contact region 32 associated with a particular patient interface device that is projected by projectors 18A and 18B onto combiners 20A and 20B based on a particular AR component data file 16. Reference numeral 34 represents an augmented image that is transmitted from the rear of combiners 20A and 20B and that is therefore viewed by the user of AR apparatus 2. In the image 34, the view 22 and the image 30 have been combined. The particular AR component data file 16 that is used to generate the image 30 may be selected by the user using input/output apparatus 6, and thus the implementation of AR apparatus 2 just described may also be used by a clinician to visualize in real-time different patient interface device geometries and styles directly on the patient's face to assess sizing, fit and potential problems.

Figure 5:
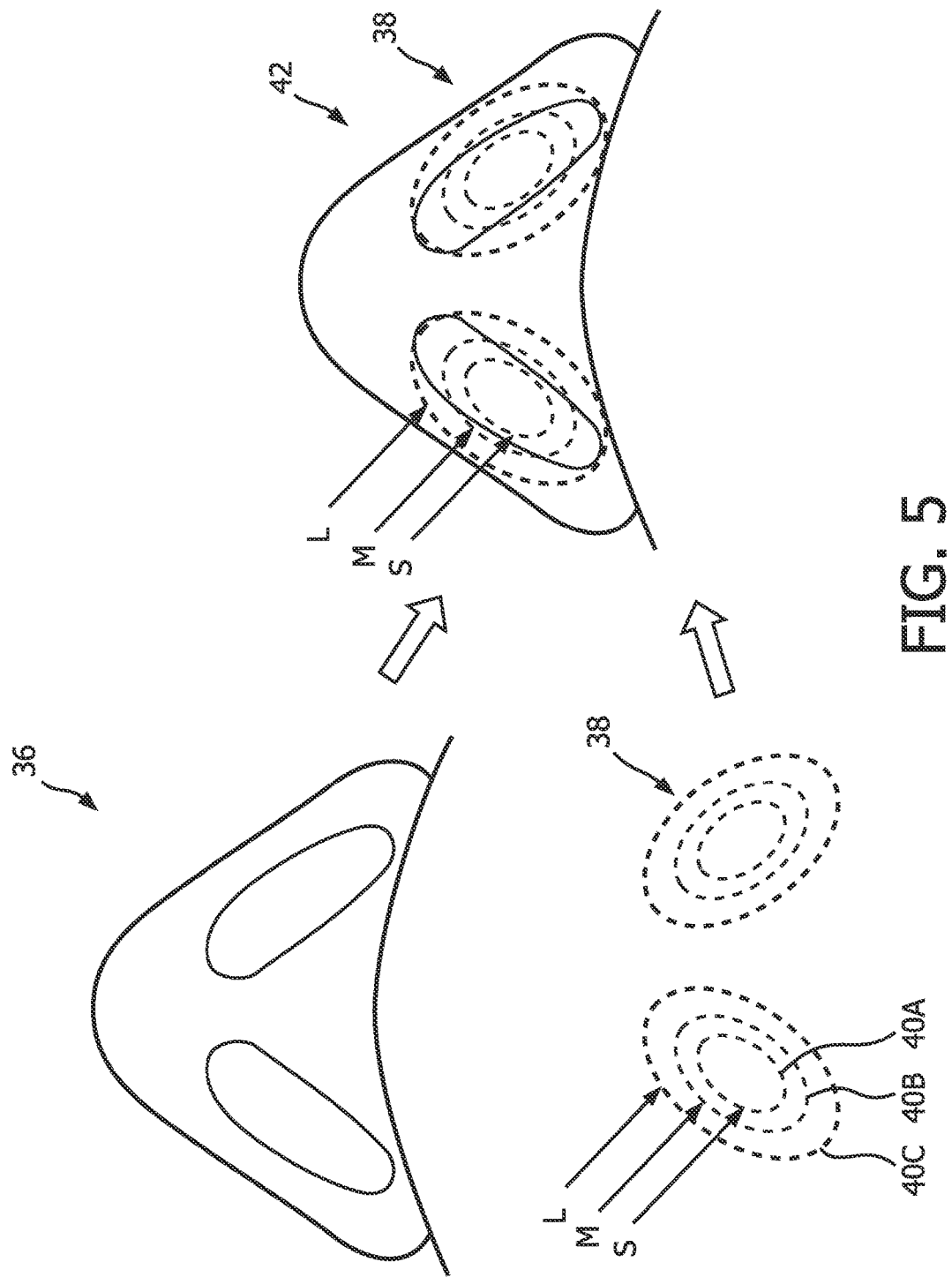

FIG. 5 is a schematic representation demonstrating the implementation of AR apparatus 2 according to still another exemplary embodiment (which may be used alone or in combination with the embodiments of FIGS. 3 and/or 4). The embodiment of FIG. 5 is similar to the embodiment of FIG. 4 in that the AR component data files 16 comprise data representing a number contact region images showing the location where various patient interface devices would actually contact the wearer's face. However, as seen in FIG. 5, AR component data file 16 shows contact regions of different sizes of the same type of interface device in a single view. In this embodiment, reference numeral 26 represents the un-augmented real world view of a patient, in this case the underside of the patient's nose. Reference numeral 38 represents an image showing multiple contact regions 40A, 40B, 40C associated with small, medium and large sizes of a particular patient interface device type that is projected by projectors 18A and 18B onto combiners 20A and 20B based on a particular AR component data file 16. Reference numeral 42 represents an augmented image that is transmitted from the rear of combiners 20A and 20B and that is therefore viewed by the user of AR apparatus 2. In the image 42, the view 36 and the image 38 have been combined. The particular AR component data file 16 that is used to generate the image 38 may be selected by the user using input/output apparatus 6, and thus the implementation of AR apparatus 2 just described may also be used by a clinician to visualize in real-time different patient interface device geometries and styles directly on the patient's face to assess sizing, fit and potential problems.

Figure 6:
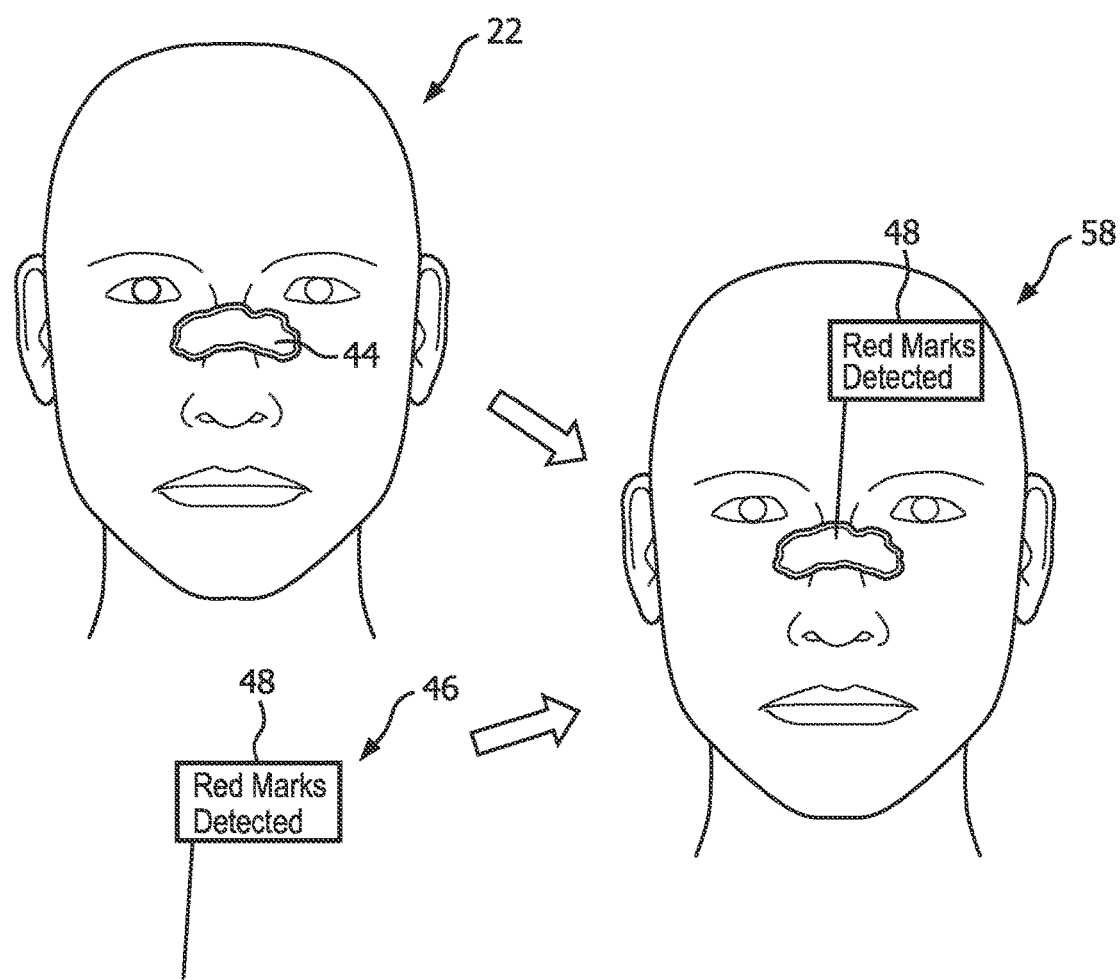

FIG. 6 is a schematic representation demonstrating the implementation of AR apparatus 2 according to another exemplary embodiment (which may be used alone or in combination with the embodiments of FIGS. 3, 4 and/or 5) wherein the AR component data files 16 comprise data representing a number of informational tags that may be rendered on the real-world view of a patient's face that indicate for the clinician potential problems areas on the patient's face/head. In this embodiment, reference numeral 22 represents the un-augmented real world view described above wherein the patient's face, in this embodiment, has a problem area 44 that may pose a problem for patient interface device use. In the illustrated example, problem 44 is a sensitive or irritated region comprising a red mark. The view 22 is provided to processor apparatus 8 for analysis thereby. In this embodiment, routines 14 include one or more routines structured to analyze the view 22 and identify problems areas therein, such as problem area 44. When a problem area 44 is identified, processor apparatus 8 causes an image 46 having an indicator 48 to be generated using one of the AR component data files 16. Processor apparatus 8 then causes the image 46 to be projected by projectors 18A and 18B onto combiners 20A and 20B such that indicator 48 will be displayed as seen in the augmented image 58 shown in FIG. 6, which combines the view 22 and image 46. Thus, the implementation of AR apparatus 2 just described may also be used by a clinician to facilitate fitting of patient interface devices by automatically identifying potential problems. As will be appreciated, this will be particularly useful to clinicians that do not have significant training and/or experience in identifying problem areas for patient interface device use.

Figure 7:
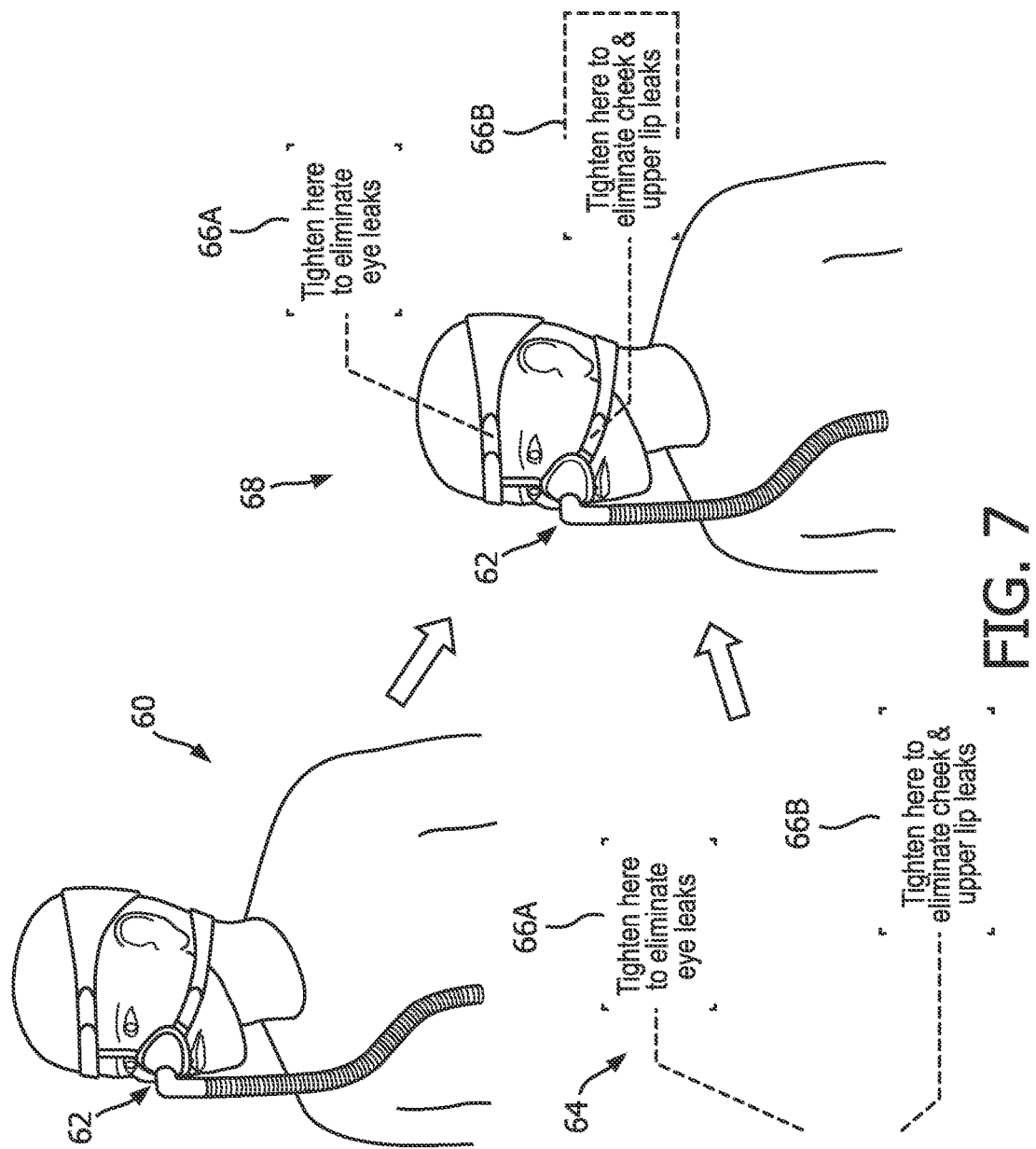

FIG. 7 is a schematic representation demonstrating the implementation of AR apparatus 2 according to yet another exemplary embodiment (which may be used alone or in combination with the embodiments of FIGS. 3, 4, 5 and/or 6) wherein the AR component data files 16 comprise data representing a number of informational tags that may be rendered on the real-world view of a patient's face that indicate for the clinician instructions for using a particular patient interface device. In this embodiment, reference numeral 60 represents the un-augmented real world view wherein the patient is wearing a particular patient interface device 62. Reference numeral 64 represents an image containing indicators 66A and 66B associated with patient interface device 62 that is projected by projectors 18A and 18B onto combiners 20A and 20B based on a particular AR component data file 16. Each indicator 66A, 66B includes an instruction for how to use a particular associated part of patient interface device 62. Reference numeral 68 represents an augmented image that is transmitted from the rear of combiners 20A and 20B and that is therefore viewed by the user of AR apparatus 2. In the image 68, the view 60 and the image 64 have been combined. The particular AR component data file 16 that is used to generate the image 64 may be selected by the user using input/output apparatus 6 based on the particular patient interface device 62 that is being worn. Thus, the implementation of AR apparatus 2 just described may also be used by a clinician to facilitate fitting of patient interface devices by automatically providing use instructions. As will be appreciated, this will be particularly useful to clinicians that do not have significant training and/or experience with particular patient interface devices.

Figure 8:
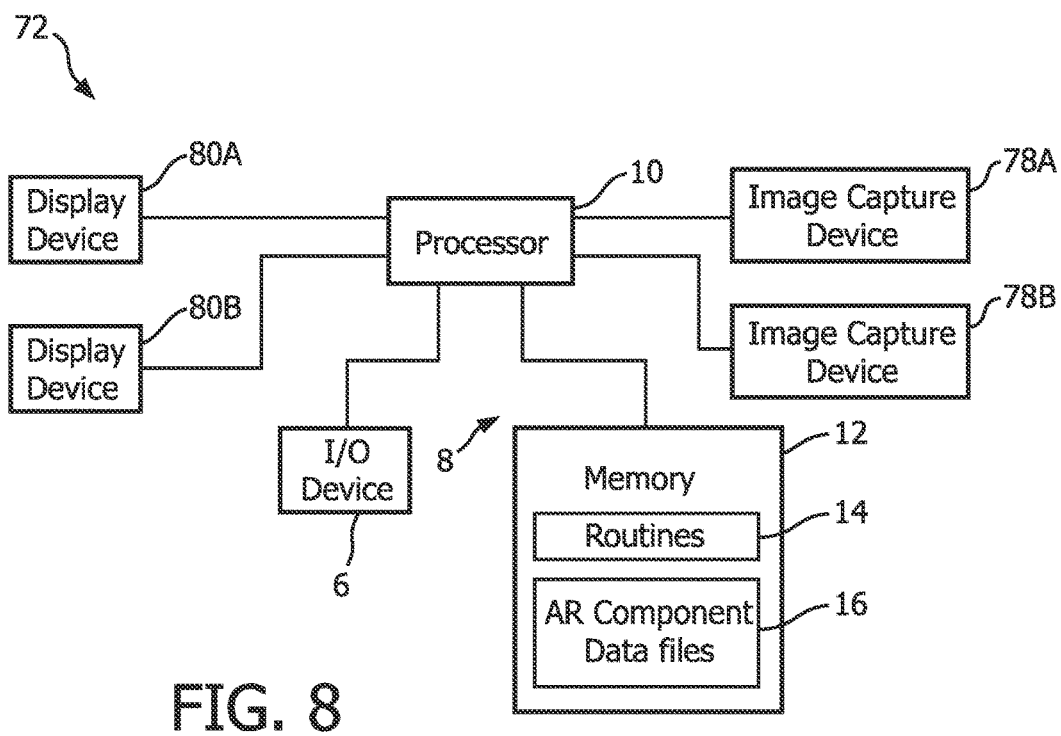
FIG. 8 is a block diagram and FIG. 9 is an isometric view of an AR apparatus for fitting a patient with a patient interface device according to an alternative non-limiting exemplary embodiment of the present invention.
Figure 9:
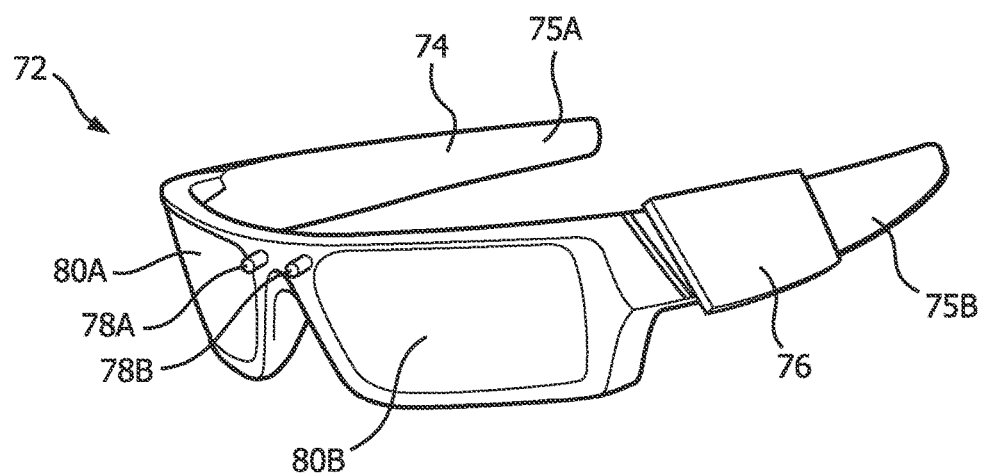

FIG. 8 is a block diagram and FIG. 9 is an isometric view of an AR apparatus 72 for fitting a patient with a patient interface device according to an alternative non-limiting exemplary embodiment of the present invention. As seen in FIG. 9, AR apparatus 72 of this non-limiting, alternative exemplary embodiment is a video system that is implemented in the form of a pair of eyeglasses having a frame member 74 having earpieces 75A and 75B. Referring to FIG. 8, AR apparatus 72 includes an input/output device 6 and a processor apparatus 8 as described elsewhere herein. A user is able to provide input (e.g., various commands as described elsewhere herein) into processor apparatus 8 using input apparatus 6, and processor apparatus 8 provides control signals to control operation of AR apparatus 72 in connection with this embodiment as described in detail herein. Processor apparatus 8 comprises a processor 10 and a memory 12 as described herein, and memory 12 has stored therein a number of routines 14 that are executable by processor 10 for controlling AR apparatus 72 in accordance with this embodiment. Memory 12 also has stored therein the database of AR component data files 16 as described elsewhere herein.

In the exemplary embodiment, processor apparatus 8 and input/output device 6 are housed by a housing member 76 that is coupled to the exterior surface of earpiece 75B.

AR apparatus 72 also includes a first image capture device 78A and a second image capture device 78B and a first display device 80A and a second display device 80B. Image capture devices 78A and 78B are any device capable of capturing an image in digital form, such as a CCD camera or an analog camera coupled to an A/D converter or a device capable of capturing a 3D image such as a Time of Flight Camera or Dual Camera system. As seen in FIG. 9, image capture devices 78A and 78B are mounted on a front surface of frame member 74 at a generally central location. First display device 80A and second display device 80B each comprise a display apparatus, such as an LCD, that is capable of displaying an image in front of a corresponding one of eyes of the wearer of AR apparatus 72. As seen in FIG. 9, first display device 80A and second display device 80B are mounted in frame member 74 at a location where traditional lenses would normally be located. Image capture devices 78A and 78B and display devices 80A and 80B are operatively coupled to processor apparatus 8 by suitable wiring (not shown) running along and/or within frame member 74 and are controlled by processor apparatus 8 to: (i) capture a video image of the physical, real-world environment being viewed by a wearer of AR apparatus 72, (ii) generate overlay imagery from the AR component data files 16, (iii) combine the captured video image and the generated overlay imagery to create an augmented video image, and (iv) cause the augmented video image to be displayed by displayed devices 80A and 80B. Thus, AR apparatus 72 is structured to implement a video AR system wherein real world views captured by image capture devices 78A and 78B may be augmented in real-time using images based on the AR component data files 16.

AR apparatus 72 may be used to implement any of the options shown in FIGS. 3-7 and described herein, except that views 22, 36 and 60 would instead represent video images captured by image capture devices 78A and 78B, images 24, 30, 38, 46, and 66A and 66B would instead represent overlay imagery generated by processor apparatus 8, and images 28, 34, 42, 58, and 68 would instead represent augmented video images displayed by display devices 80A and 80B.

Figure 10:
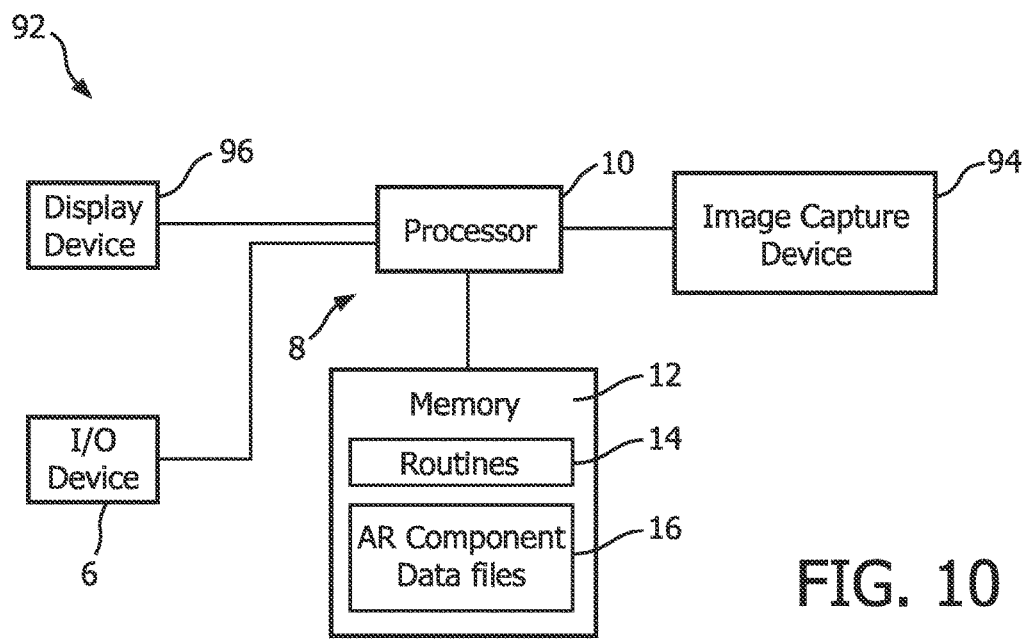
FIG. 10 is a block diagram of an AR apparatus for fitting a patient with a patient interface device according to another alternative non-limiting exemplary embodiment of the present invention.

FIG. 10 is a block diagram of an AR apparatus 92 for fitting a patient with a patient interface device according to another alternative non-limiting exemplary embodiment of the present invention. AR apparatus 92 of this non-limiting, alternative exemplary embodiment is a video system that is implemented in the form of computing device such as, without limitation, a PC, smartphone or tablet computer. AR apparatus 92 includes an input/output device 6 and a processor apparatus 8 as described elsewhere herein. A user is able to provide input (e.g., various commands as described elsewhere herein) into processor apparatus 8 using input apparatus 6, and processor apparatus 8 provides control signals to control operation of AR apparatus 92 in connection with this embodiment as described in detail herein. Processor apparatus 8 comprises a processor 10 and a memory 12 as described herein, and memory 12 has stored therein a number of routines 14 that are executable by processor 10 for controlling AR apparatus 92 in accordance with this embodiment. Memory 12 also has stored therein the database of AR component data files 16 as described elsewhere herein.

AR apparatus 92 also includes an image capture device 94 and a display device 96. Image capture device 94 is any device capable of capturing an image in digital form, such as a CCD camera found on many smartphones and tablet computers, or an analog camera coupled to an A/D converter, or a device capable of capturing a 3D image such as a Time of Flight Camera or Dual Camera system. Display device 96 comprises a display apparatus, such as an LCD found on many smartphones and tablet computers, that is capable of displaying an image. Image capture device 94 and display device 96 are operatively coupled to processor apparatus 8 are controlled by processor apparatus 8 to: (i) capture a video image of the physical, real-world environment at which image capture device is pointed, (ii) generate overlay imagery from the AR component data files 16, (iii) combine the captured video image and the generated overlay imagery to create an augmented video image, and (iv) cause the augmented video image to be displayed by displayed device 96. Thus, AR apparatus 92 is structured to implement a video AR system wherein real world views captured by image capture device 94 may be augmented in real-time using images based on the AR component data files 16.

Figure 11:
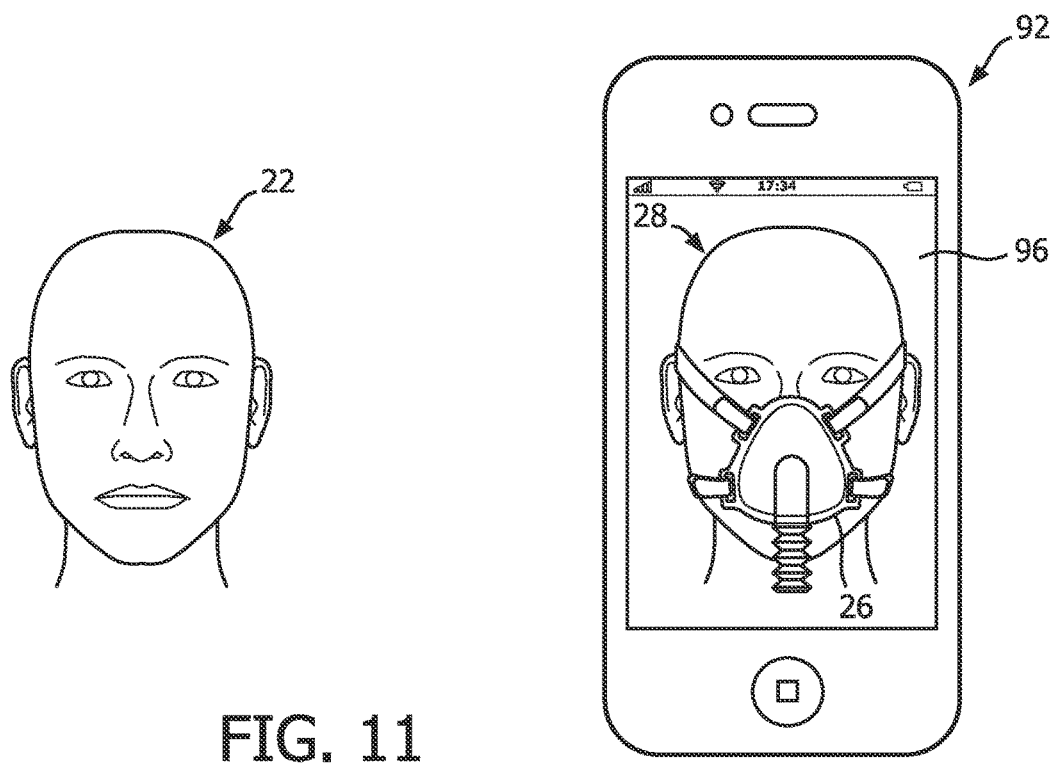
FIG. 11 is a schematic representation demonstrating the implementation of the AR apparatus of FIG. 10 according to an exemplary embodiment.

AR apparatus 92 may be used to implement any of the options shown in FIGS. 3-7 and described herein, except that views 22, 36 and 60 would instead represent video images captured by image capture device 94, images 24, 30, 38, 46, and 66A and 66B would instead represent overlay imagery generated by processor apparatus 8, and images 28, 34, 42, 58, and 68 would instead represent augmented video images displayed by display device 96. One example of such an implementation is shown in FIG. 11 (wherein AR apparatus 92 is in the form of a smartphone).

In still another embodiment, AR apparatus 92 may be implemented in the form of a first person embodiment such that the augmented reality image that is displayed would show the user the renderings on his or her own face. Such a first person embodiment could be implemented in AR apparatus 92 by using a front facing camera as image capture device 94. Another first person embodiment may be an optical system employing a smart mirror where in augmented reality imagery as described herein is added to the image as reflected by the mirror.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An augmented reality apparatus for facilitating a patient interface device fitting process, comprising:
    means for providing a real-time image of the patient; and
    a processor apparatus storing a plurality of augmented reality component data files, the plurality of augmented reality component data files including, for each of a plurality of patient interface devices comprising a plurality of different sizes of a particular patient interface device type, contact region image data representing an image of a contact region showing only where the patient interface device would actually contact a wearer's face and not representing an image of the patient interface device itself, the processor apparatus being configured to cause an augmented real-time image to be created and transmitted by the augmented reality apparatus by augmenting the real-time image using the contact region image data of at least one of the augmented reality component data files, wherein the augmented real-time image comprises one or more of the contact regions rendered on the real-time image, and wherein the processor apparatus is configured to cause the augmented real-time image to be created and transmitted by the augmented reality apparatus by augmenting the real-time image using the contact region image data of each of the plurality of different sizes of the particular patient interface device type simultaneously.

2. An augmented reality apparatus according to claim 1, wherein the means for providing a real-time image comprises a combiner, wherein the augmented reality apparatus includes a projector, and wherein the processor apparatus is structured and configured to cause the augmented real-time image to be created by causing the projector to create and transmit to the combiner a supplemental image which is combined with the real-time image.

3. An augmented reality apparatus according to claim 2, wherein the augmented reality apparatus is a head mounted display apparatus, wherein the combiner is a partially transmissive and partially reflective lens, and wherein the projector is mounted on a frame member of the head mounted display apparatus in a manner where in the supplemental image is transmitted to a reflective surface of the lens.

4. An augmented reality apparatus according to claim 3, wherein the head mounted display apparatus is a pair of eyeglasses.

5. An augmented reality apparatus according to claim 1, wherein the means for providing a real-time image comprises an image capture device, wherein the augmented reality apparatus includes a display device, and wherein the processor apparatus is structured and configured to cause the augmented real-time image to be created by creating a supplemental image using the least one of the augmented reality component data files, supplementing the real-time image using the supplemental image to create the augmented real-time image, and causing the augmented real-time image to be transmitted by the display device.

6. An augmented reality apparatus according to claim 1, wherein the augmented reality component data files further include data that represents a 2D or 3D patient interface device image, wherein the processor apparatus is configured to cause a second augmented real-time image to be created and transmitted by the augmented reality apparatus by augmenting the real-time image using at least one of the augmented reality component data files, and wherein the second augmented real-time image comprises the 2D or 3D patient interface device image rendered on the real-time image.

7. An augmented reality apparatus according to claim 1, wherein the augmented reality component data files further include data that represents an instructional tag image including text indicating a potential problem area, wherein the processor apparatus is configured to cause a second augmented real-time image to be created and transmitted by the augmented reality apparatus by augmenting the real-time image using at least one of the augmented reality component data files, and wherein the second augmented real-time image comprises the instructional tag image rendered on the real-time image.

8. An augmented reality apparatus according to claim 1, wherein the augmented reality component data files further include data that represents an instructional tag image including text indicating instructions for using a particular one of the patient interface devices, and wherein the second augmented real-time image comprises the instructional tag image rendered on the real-time image.

9. An augmented reality patient interface device fitting method, comprising:
   storing in a processor apparatus of an augmented reality apparatus a plurality of augmented reality component data files, the plurality of augmented reality component data files including, for each of a plurality of patient interface devices comprising a plurality of different sizes of a particular patient interface device type, contact region image data representing an image of a contact region showing only where the patient interface device would actually contact a wearer's face and not representing an image of the patient interface device itself;
   providing in the augmented reality apparatus a real-time image of a patient; and
   creating and transmitting by the augmented reality apparatus an augmented real-time image by augmenting the real-time image using the contact region image data of at least one of the augmented reality component data files, wherein the augmented real-time image comprises one or more of the contact regions rendered on the real-time image, wherein the creating and transmitting comprises augmenting the real-time image using the contact region image data of each of the plurality of different sizes of the particular patient interface device type simultaneously.

10. An augmented reality patient interface device fitting method according to claim 9, wherein the providing the real-time image employs a combiner, and wherein the creating and transmitting the augmented real-time image comprises causing a projector to create and transmit to the combiner a supplemental image which is combined with the real-time image.

11. An augmented reality patient interface device fitting method according to claim 9, wherein the providing the real-time image employs an image capture device, and wherein the creating and transmitting the augmented real-time image comprises creating a supplemental image using the least one of the augmented reality component data files, supplementing the real-time image using the supplemental image to create the augmented real-time image, and causing the augmented real-time image to be transmitted by a display device.

12. An augmented reality patient interface device fitting method according to claim 9, wherein the augmented reality component data files further include data that represents a 2D or 3D patient interface device image, wherein the method includes causing a second augmented real-time image to be created and transmitted by the augmented reality apparatus by augmenting the real-time image using at least one of the augmented reality component data files, and wherein the second augmented real-time image comprises the 2D or 3D patient interface device image rendered on the real-time image.

13. An augmented reality patient interface device fitting method according to claim 9, wherein the augmented reality component data files further include data that represents an instructional tag image including text indicating a potential problem area, wherein the method includes causing a second augmented real-time image to be created and transmitted by the augmented reality apparatus by augmenting the real-time image using at least one of the augmented reality component data files, and wherein the second augmented real-time image comprises the instructional tag image rendered on the real-time image.

14. An augmented reality patient interface device fitting method according to claim 9, wherein the augmented reality component data files further include data that represents an instructional tag image including text indicating instructions for using a particular one of the patient interface devices, wherein the method includes causing a second augmented real-time image to be created and transmitted by the augmented reality apparatus by augmenting the real-time image using at least one of the augmented reality component data files, and wherein the second augmented real-time image comprises the instructional tag image rendered on the real-time image.

* * * * *